United States Patent [19]

Yan

[11] Patent Number: 5,268,155
[45] Date of Patent: Dec. 7, 1993

[54] CLEAN UP OF ETHANOLAMINE TO IMPROVE PERFORMANCE AND CONTROL CORROSION OF ETHANOLAMINE UNITS

[75] Inventor: Tsoung Y. Yan, Philadelphia, Pa.

[73] Assignee: Mobil Oil Corporation, Fairfax, Va.

[21] Appl. No.: 809,034

[22] Filed: Dec. 16, 1991

Related U.S. Application Data

[60] Continuation of Ser. No. 542,282, Jun. 22, 1990, abandoned, which is a continuation of Ser. No. 288,392, Dec. 22, 1988, abandoned, which is a division of Ser. No. 113,316, Oct. 28, 1987, Pat. No. 4,795,565.

[51] Int. Cl.⁵ .......................... C01B 17/06; C02F 1/42
[52] U.S. Cl. ................................ 423/229; 210/683; 210/685; 210/681; 521/26
[58] Field of Search ..................... 521/26, 28; 423/229; 210/681, 683, 685

[56] References Cited

U.S. PATENT DOCUMENTS

| | | | |
|---|---|---|---|
| Re. 29,128 | 10/1977 | Homberg et al. | 423/229 |
| 2,797,188 | 6/1957 | Taylor, Jr. et al. | 423/229 |
| 3,385,787 | 5/1968 | Crits et al. | 210/32 |
| 3,554,691 | 1/1971 | Kuo et al. | 423/229 |
| 3,928,192 | 12/1975 | Katzakian, Jr. et al. | 210/30 |
| 4,071,602 | 1/1978 | Pearce et al. | 423/228 |
| 4,152,217 | 5/1979 | Eisenberg et al. | 423/229 |
| 4,477,419 | 10/1984 | Pearce et al. | 423/243 |
| 4,652,352 | 3/1987 | Saieva et al. | 204/105 R |
| 4,795,565 | 1/1989 | Yan | 210/669 |
| 4,820,421 | 4/1989 | Auerswald | 210/670 |
| 4,970,344 | 11/1990 | Keller | 561/497 |
| 5,006,258 | 4/1991 | Veatch et al. | 210/677 |
| 5,045,291 | 9/1991 | Keller | 423/228 |

Primary Examiner—Peter F. Kulkosky
Attorney, Agent, or Firm—Alexander J. McKillop; Dennis P. Santini; Robert B. Furr, Jr.

[57] ABSTRACT

A process is disclosed for the removal of heat stable salts from ethanolamine gas purification process units using ion-exchange resins and for regenerating said ion-exchange resins in-situ.

38 Claims, 1 Drawing Sheet

CLEAN UP OF ETHANOLAMINE TO IMPROVE PERFORMANCE AND CONTROL CORROSION OF ETHANOLAMINE UNITS

CROSS-REFERENCE TO RELATED APPLICATIONS

This is a continuation of copending application Ser. No. 07/542,282, filed on Jun. 22, 1990, now abandoned, which is a continuation of U.S. application Ser. No. 288,392, filed Dec. 22, 1988, now abandoned which is a division of U.S. application Ser. No. 113,316, filed Oct. 28, 1987, now U.S. Pat. No. 4,795,565.

BACKGROUND OF THE INVENTION

1. Field of the Invention

The present invention relates to a process for removing heat-stable salts from ethanolamine gas purification process units. Ethanolamine units remove $H_2S$ and $CO_2$ from gaseous process streams. One objective of the invention is to improve the gas purification performance of the ethanolamine unit. Another objective is to control the corrosion rate of the unit. Both objectives are accomplished by the removal of heat-stable salts accumulating in the ethanolamine gas purification process units. For the purpose of this application, it is understood that the term "ethanolamine" is a generic term including, but not limited to, monoethanolamine, diethanolamine, triethanolamine and methyl diethanolamine.

2. Description of the Prior Art

The removal of hydrogen sulfide from gaseous streams, such as the waste gases liberated in the course of various chemical and industrial processes, for example, in the pulping of wood, natural gas and crude oil production and in petroleum refining, has become increasingly important in combating atmospheric pollution. Hydrogen sulfide-containing gases not only have an offensive odor, but such gases may cause damage to vegetation, painted surfaces and wildlife, as well as constitute a significant health hazard to humans. Government-wide regulations have increasingly imposed continuously lower tolerances on the content of hydrogen sulfide which can be vented to the atmosphere, and it is now imperative in many localities to remove virtually all the hydrogen sulfide under the penalty of an absolute ban on continuing operation of a plant or the like which produces the hydrogen sulfide-containing gaseous stream. Solutions of water and one or more of the ethanolamines are widely used in industry to remove hydrogen sulfide and carbon dioxide from gaseous streams.

Corrosion in ethanolamine units significantly increases both operating and maintenance costs. The mechanisms of corrosive attack include corrosion, corrosion-erosion and stress-corrosion cracking. Corrosion control techniques include the use of more expensive corrosion and erosion resistant materials, continuous periodic removal of corrosion-promoting agents in suspended solids from the solution by filtration or activated carbon adsorption and addition of corrosion inhibitors. (See Kohl, A. L. and Reisenfeld, F. C., Gas Purification, Gulf Publishing Co., Houston, 1979, pg. 91–105).

While corrosion resistant materials of construction and chemical corrosion inhibitors may reduce corrosive attack, neither addresses the progressive degradation in process unit performance caused by the accumulation of heat stable salts in the ethanolamine solution.

It is known that these heat stable salts may be separated from the enthanolamine solution by distillation. However, such separation is limited to relatively mild conditions of temperature and pressure to avoid thermal degradation of the ethanolamine solution. For a survey of the chemistry, engineering, and operational aspects of ethanolamine gas purification. (See K. F. Butwell, D. J. Kubek, and P. W. Sigmund, "Alkanolamine Treating", HYDROCARBON PROCESSING, Mar., 1982.)

SUMMARY OF THE INVENTION

It is an object of the invention to improve the performance of ethanolamine gas purification units. Additionally, it is an object of the invention to control the corrosion rate in ethanolamine gas purification units.

The present invention provides a process for removing heat stable salts which accumulate in ethanolamine gas purification process units. Ethanolamine is most often used to purify hydrocarbon gases by removing $H_2S$ and $CO_2$. The ethanolamine is used as a 20–50% aqueous solution. The $H_2S$ and $CO_2$ in the hydrocarbon gas react with ethanolamine and are removed. While there are various ethanolamines, (such as monoethanolamine (MEA), diethanolamine (DEA) and triethanolamine (TEA) and methyl diethanolamine (MDEA), which can be used in this application, it is preferred to employ the subject invention with an aqueous solution comprising an ethanolamine which boils at above 400° F. at atmospheric pressure. The choice of ethanolamine depends on the particular situations. For purification of natural gas with high $CO_2/H_2S$ ratio, diethanolamine is frequently the choice.

In the course of operation, some heat stable salts accumulate in the system. These include $SO_4^=$, $Cl^-$, $K^+$ and $Na^+$. It is known that these heat stable salts impair the performance and increase the corrosion rate of the ethanolamine unit.

In a monoethanolamine system, four ethanolamine solution purification techniques are commonly available to remove precipitates and heavy sludges: (1) settling, (2) filtration, (3) distillation and (4) activated carbon adsorption. While settling is an effective separation technique, it may not be economically feasible to construct a settling vessel large enough to provide the required residence time. Filtration is also an effective separation technique, but is generally disfavored due to high maintainance costs. The most commonly used purification technique is the distillation of an monoethanolamine slip stream.

While distillation is effective for monoethanolamine systems, it is less attractive for application to diethanolamine and triethanolamine systems due to temperature limitations. The temperatures required for the purification of DEA, TEA OR MDEA by distillation lead to thermal degradation of the amine. These undesired degradation products boil in a narrow range of temperatures around the boiling point of the associated amine. This reaction makes separation by distillation extremely difficult. To avoid thermal degradation of diethanolamine and triethanolamine, these solutions must be vacuum distilled.

Equipment and operating costs for vacuum distillation are generally higher than those associated with distillation under positive pressure. However, the costs are dramatically higher for ethanolamine regeneration facilities associated with natural gas purification, where the diethanolamine or monoethanolamine solution to be distilled must be depressured from in excess of about 700 psig to below atmospheric pressure, distilled under a vacuum, and then pumped back up to about 700 psig to reenter the ethanolamine gas purification system. Consequently, such purification by distillation is disfavored in industry.

In accordance with this invention, it has been found that the extraction of heat stable salts from aqueous ethanolamine solutions using certain ion-exchange resins can be carried out substantially independently of pressure. As a result, it is an object of this invention to remove contaminants from the ethanolamine solution at the full operating pressure of the associated ethanolamine gas purification unit using ion exchange resins, thus enhancing unit performance, reducing energy consumption and controlling the process unit corrosion rate. It is a further object of this invention to regenerate these ion exchange resins in place.

DETAILED DESCRIPTION OF THE DRAWING

Figure 1:
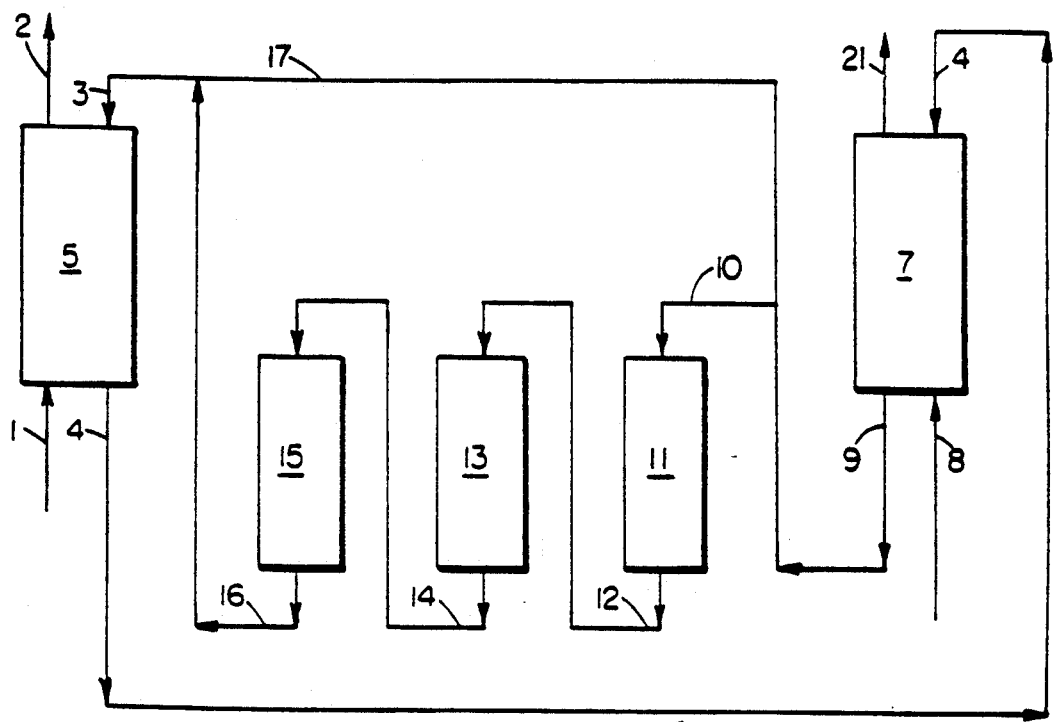
FIG. 1 is a schematic diagram of the present invention illustrating the routes of the various process streams during normal process unit operation.

Referring to FIG. 1, the crude gas 1 containing $CO_2$ and/or $H_2S$ is passed upwardly through the ethanolamine absorber column 5, where the crude gas is countercurrently contacted with lean ethanolamine solution 3. The lean ethanolamine solution 3 absorbs the $CO_2$ and $H_2S$, thereby purifying the gas. The purified gas stream 2 exits the top of the ethanolamine absorber column 5. Upon absorption of $CO_2$ and $H_2S$, the lean ethanolamine solution 3 becomes a rich ethanolamine solution 4.

The rich ethanolamine 4 is charged to the top of a stripper tower 7 and is stripped with steam 8 at about 240° F. to remove the $CO_2$ and $H_2S$ 21. Upon stripping, the rich ethanolamine 4 becomes lean ethanolamine 9. The lean ethanolamine 9 exits the bottom of the steam stripper tower 7 and is returned to the absorber 5 to start another cycle of absorption/stripping. However, a fraction of the lean ethanolamine 10 is passed through a filter medium 11 to remove the solid suspension. The filtered stream 12 is fed to a second vessel 13 containing strongly basic anionic resins to remove anionic species, such as $SO_4^=$ and $Cl^-$. The effluent stream 14 then flows to a vessel containing cationic resins 15 to remove cations such as $Na^+$, $K^+$, $Fe^{++}$, etc. This cleaned lean ethanolamine solution 16 is combined with lean ethanolamine 17 to become the lean ethanolamine feed stream 3 for the ethanolamine absorber 5. In a separate operation, the ion exchange resins are regenerated from time to time for reuse.

Figure 2:
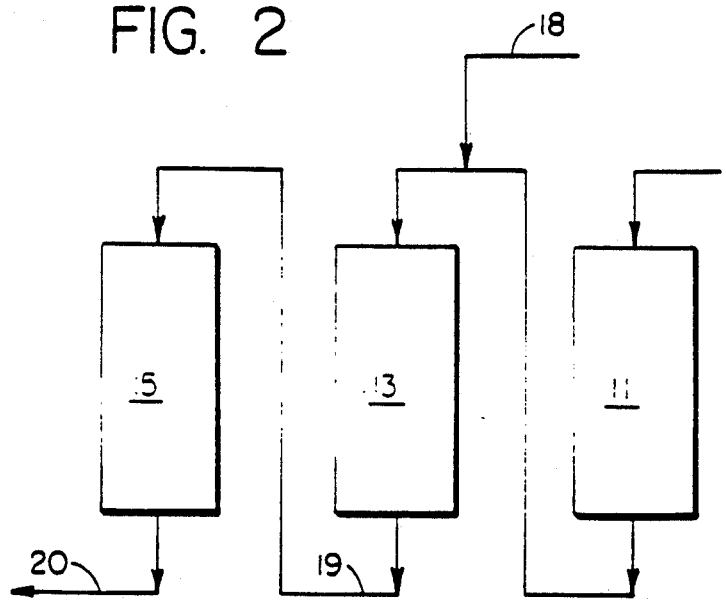
FIG. 2 is a schematic diagram of the present invention illustrating the routes of the various process streams during regeneration of the ion-exchange resins.

Turning now to FIG. 2, the regeneration solution comprising an aqueous solution of $(NH_4)_2CO_3$, $NH_4HCO_3$, $NH_4OH$ or a mixture thereof 18 is fed to the anionic IX ion-exchange vessel 13. The effluent 19 is fed to the cationic IX ion-exchange vessel 15. The effluent liquid 20 may then be disposed of or stripped with steam for reuse.

The fraction of lean ethanolamine which should be cleaned through the ion exchange varies with the extent of contamination. It can range between 0 and 100%, but 5-20% is preferred. It should be pointed out that this clean up loop should be operated continuously to ensure smooth operation. However, it can be operated intermittently. For example, the clean up loop can be shut down during the regeneration of the anionic or cationic resins and/or during filter change over.

While it is preferred for the anionic resins to precede the cationic resins in the cleanup loop, it should be understood that the reverse order will also achieve the desired result. Further, the resins may be contained in separate vessels or in separate beds in a single vessel.

The anionic IX resin used must be strongly basic because the ethanolamine solution itself is highly basic. The preferred anionic resins contain quaternary ammonium functional groups as the active ion constituent. Typical structures are:

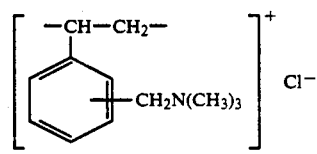

TYPE I

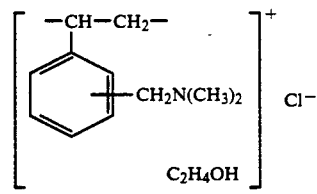

TYPE II

Because of its stability, Type I is more preferred. The preferred commercially anionic resins include: Dowex 21K; Dowex MS-1; Amberlite IRA 400, 900, 910; and Ionac A-540 and A-641. The anion IX may be used in the gel, semiporous and macroporous structural forms.

The cationic exchange resins must be of the sulfonic and carboxylic types having the following structures:

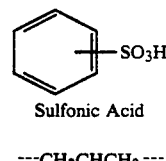

Sulfonic Acid

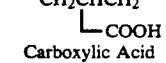

Carboxylic Acid

Because of its stability, sulfonic acid is preferred. The preferred commercially available anionic resins include Amberlite IR-120; Amberlite IR-200; Amberlist-15; Amberlist-1010; Dowex 50; CCR-1; Ionac C-240; Ionac C-249 and Ionac C-253.

In a preferred embodiment, the anionic IX exchange resin is followed by the cationic IX exchange resin. The exchange resins may be contained in separate vessels or in a single mixed bed vessel. While it is preferred to arrange the exchange resins in series with the cationic IX exchange resin following the anionic IX exchange resin, the resins may also be placed in series with the anionic IX exchange resin following the cationic IX exchange resin.

The mixed bed in a single vessel is made up of two zones, in series, each containing a different type of ion exchange resin, for example, anionic exchange resin followed by cationic exchange resin.

The relative amount of anionic and cationic exchange resins required is calculated as follows:

$$R = \frac{\text{Anionic IX, g}}{\text{Cationic IX, g}}$$

$$= \frac{\text{Anionic Impurities in the Solution, mmol/liter}}{\text{Cationic Impurities in the Solution, mmol/liter}} \times \frac{\text{Capacity of Cationic IX, meq/g}}{\text{Capacity of Anionic IX, meq/g}}$$

Typically, the range of values for R is between about 1 and about 1.2.

In accordance with the invention, it has been discovered that $(NH_4)_2CO_3$, $NH_4HOO_3$, $NH_4OH$ and their mixtures can be used to regenerate both the anionic and cationic exchange resins in series. The regeneration solution is thus passed over the anionic resins and then over the cationic resins in the same order as the lean ethanolamine solution passes through the system during normal unit operation. Most importantly, the counter ions remaining in the ion exchange resins after regeneration, namely, $CO_3^-$ in the anionic and $NH_4^+$ in the cationic, will be removed by exchange with the impurities in the ethanolamine-water stream. The counter ions will then be stripped out of the ethanolamine solution downstream in the ethanolamine unit's stripper tower. Thus the ion exchange resins may be put back into service immediately following regeneration without further treatment. This is advantageous both from the economic and environmental points of view. The total concentrations of $(NH_4)_2CO_3$, $NH_4HCO_3$ and $NH_4OH$ can be 0.1 to 5 moles per liter, preferably 0.5 to 2 moles per liter.

What is claimed is:

1. A process for removing heat stable salts from an ethanolamine-water solution having ethanolamine concentration sufficient for effective sorption of acid gases comprising the steps of:
   (a) filtering said ethanolamine-water solution to remove suspended paticulate;
   (b) contacting said filtered ethanolamine-water solution with an anionic ion-exchange resin;
   (c) contacting said ethanolamine-water solution with a cationic exchange resin;
   (d) regenerating said ion-exchange resins in-situ with an aqueous solution of $(NH_4)_2HCO_3$, $NH_4HCO_3$, $NH_4OH$, or mixture thereof wherein said aqueous regeneration solution is substantially free from species which form heat stable salts in said ethanolamine-water solution to minimize accumulation of heat stable salts in said ethanolamine-water solution; and
   (e) recycling said ethanolamine-water solution through steps (b) and (c) with said regenerated ion-exchange resins of step (d) in the absence of an ion-exchange resin rinsing step for removing residual regeneration solution from said ion-exchange resins wherein heat stable salt content is reduced as compared to the same method using other caustic regenerants.

2. The process of claim 1 wherein said ethanolamine-water solution comprises a solution of water and one or more of the group comprising monoethanolamine, di-ethanolamine, triethanolamine, or methyl diethanolamine.

3. The process of claim 1 wherein said ethanolamine-water solution comprises a solution of water and an ethanolamine which boils at above 400° F. at atmospheric pressure.

4. The process of claim 1 wherein said ethanolamine-water solution comprises a solution of water and diethanolamine.

5. The process of claim 1 wherein said ethanolamine-water solution comprises a solution of water and triethanolamine.

6. The process of claim 1 wherein said anionic ion-exchange resin contains a quaternary ammonium functional group as the active ion constituent.

7. The process of claim 1 wherein said cationic exchange resin comprises sulfonic or carboxylic acid or a mixture thereof.

8. The process of claim 2 wherein said cationic exchange resin comprises sulfonic or carboxylic acid or a mixture thereof.

9. The process of claim 1 wherein said anionic and said cationic ion-exchange resins are placed in separate beds, one above the other, in a single vessel.

10. The process of claim 1 wherein said anionic and said cationic ion-exchange resins are placed in separate vessels.

11. The process of claim 1 further comprising contacting said ethanolamine-water solution with an anionic ion-exchange resin prior to contacting said ethanolamine-water solution with a cationic ion-exchange resin.

12. The process of claim 1 further comprising contacting said ethanolamine-water solution with a cationic ion-exchange resin prior to contacting said ethanolamine-water solution with a cationic ion-exchange resin.

13. A process for removing salts from an ethanolamine-water solution having ethanolamine concentration sufficient for effective sorption of acid gases comprising the steps of:
   (a) filtering said ethanolamine-water solution to remove suspended particulate;
   (b) contacting said filtered ethanolamine-water solution with an anionic ion-exchange resin;
   (c) contacting said ethanolamine-water solution with a cationic exchange resin;
   (d) regenerating said ion-exchange resins in-situ to restore the ion exchange capacity of said ion-exchange resins while minimizing accumulation of heat stable salts in said ethanolamine-water solution by
      (i) contacting said anionic ion-exchange resin with an aqueous solution of $(NH_4)_2HCO_3$, $NH_4HCO_3$, $NH_4OH$, or a mixture thereof whereby counter ions are deposited on said anionic ion-exchange resin;
      (ii) separating said solution from said anionic ion-exchange resin with
      (iii) contacting said cationic ion-exchange resin with said aqueous solution of $(NH_4)_2HCO_3$, $NH_4HCO_3$, $NH_4OH$, or a mixture thereof whereby counter ions are deposited on said cationic ion-exchange resin;
      (iv) separating said cationic ion-exchange resin from said solution; and
      (v) recycling at least a portion of said ethanolamine-water solution to steps (b) and (c) for contact with said regenerated ion-exchange resins of step (d) in the absence of an ion exchange resin rinsing step for removing residual regeneration solution from said ion-exchange resin wherein heat stable salt content is reduced as compared to the same method using other caustic regenerants, and whereby said counter ions are removed from said ion exchange resins by exchange with impurities in said ethanolamine-water solution; and (vi) stripping said counter ions from said ethanolamine solution.

14. The process of claim 13 wherein the total concentration of $(NH_4)_2HCO_3$, $NH_4HCO_3$, and $NH_4OH$ is between about 0.1 and about 5 moles per liter.

15. The process of claim 13 wherein the total concentration of $(NH_4)_2HCO_3$, $NH_4HCO_3$, and $NH_4OH$ is between about 0.5 and about 2 moles per liter.

16. The process of claim 14 wherein the total concentration of $(NH_4)_2HCO_3$, $NH_4HCO_3$, and $NH_4OH$ is between about 0.1 and about 5 moles per liter.

17. The process of claim 14 wherein the total concentration of $(NH_4)_2HCO_3$, $NH_4HCO_3$, and $NH_4OH$ is between about 0.5 and about 2 moles per liter.

18. A continuous process for purifying a gas stream containing $CO_2$, $H_2S$ or both, comprising the steps of:

(a) contacting said gas stream with an ethanolamine-water solution, said ethanolamine-water solution having ethanolamine concentration sufficient for effective sorption of $CO_2$, $H_2S$ or both;

(b) contacting said ethanolamine-water solution with an anionic ion-exchange resin;

(c) contacting said ethanolamine-water solution with a cationic exchange resin;

(d) regenerating said ion-exchange resins in-situ with an aqueous solution of $(NH_4)_2HCO_3$, $NH_4HCO_3$, $NH_4OH$, or a mixture thereof to minimize accumulation of heat stable salts in said ethanolamine-water solution whereby counter ions are deposited on said anionic and said cationic exchange resins; and (e) repeating steps (a), (b), and (c) with the provisoes that steps (b) and (c) are conducted with the regenerated ion-exchange resins of step (d), that at least a portion of said ethanolamine-water solution is recycled to step (a), that said counter ions are removed from said ion exchange resins by exchange with impurities in said ethanolamine-water solution, that the regenerated ion-exchange resins of step (d) are not rinsed to remove said aqueous solution of step (d), and that said counter ions are subsequently stripped from said ethanolamine-water solution wherein heat stable salt content is reduced as compared to the same method using other caustic regenerants.

19. The process of claim 18 wherein said ethanolamine-water solution comprises a solution of water and one or more of the group comprising monoethanolamine, diethanolamine, triethanolamine, or methyl diethanolamine.

20. A continuous process for purifying a gas stream containing $CO_2$, $H_2S$ or both, comprising the steps of:

(a) splitting said gas stream into a bypass stream and a slip stream, said slip stream comprising between 0 and 100% of the total mass flow of said gas stream;

(b) contacting said slip stream with an ethanolamine-water solution, said ethanolamine-water solution having ethanolamine concentration sufficient for effective sorption of $CO_2$, $H_2S$ or both;

(c) contacting said ethanolamine-water solution with an anionic ion-exchange resin;

(d) contacting said ethanolamine-water solution with a cationic ion-exchange resin;

(e) regenerating said ion-exchange resins in-situ with an aqueous solution of $(NH_4)_2HCO_3$, $NH_4HCO_3$, $NH_4OH$, or a mixture thereof to minimize accumulation of heat stable salts in said ethanolamine-water solution; and (f) repeating steps (c) and (d) with the provisoes that steps (c) and (d) are conducted with the regenerated ion-exchange resins of step (e), that at least a portion of said ethanolamine-water solution is recycled to step (b), that said counter ions are removed from said ion-exchange resins by exchange with impurities in said ethanolamine-water solution, that the regenerated ion-exchange resins of step (d) are not rinsed to remove said aqueous solution of step (d), and that said counter ions are subsequently stripped from said ethanolamine-water solution wherein heat stable salt content is reduced as compared to the same method using other caustic regenerants.

21. The process of claim 20 wherein said slip stream comprises from about 5 to about 20% of the mass flow of said gas stream of step (a).

22. The process of claim 20 wherein said ethanolamine-water solution comprises a solution of water and one or more of the group comprising monoethanolamine, diethanolamine, triethanolamine, or methyl diethanolamine.

23. A process for removing heat stable salts from an ethanolamine-water solution having ethanolamine concentration sufficient for effective sorption of acid gases comprising the steps of:

(a) filtering said ethanolamine-water solution to remove suspended particulate;

(b) contacting said filtered ethanolamine-water solution with an anionic ion-exchange resin;

(c) contacting said ethanolamine-water solution with a cationic exchange resin;

(d) regenerating said ion-exchange resins in-situ with an aqueous solution of $(NH_4)_2HCO_3$, $NH_4HCO_3$, $NH_4OH$, or a mixture thereof wherein said aqueous regeneration solution is substantially free from species which form heat stable salts in said ethanolamine-water solution to minimize accumulation of heat stable salts in said ethanolamine-water solution; and (e) recycling said ethanolamine-water solution through steps (b) and (c) with said regenerated ion-exchange resins of step (d) in the absence of an ion-exchange resin rinsing step for removing residual regeneration solution from said ion-exchange resins wherein heat stable salt content is reduced as compared to the same method using other caustic regenerants.

24. The process of claim 23 wherein said ethanolamine-water solution comprises a solution of water and one or more of the group consisting of monoethanolamine, diethanolamine, triethanolamine, or methyl diethanolamine.

25. The process of claim 23 wherein said ethanolamine-water solution comprises a solution of water and an ethanolamine which boils at above 400° F. at atmospheric pressure.

26. The process of claim 23 wherein said ethanolamine-water solution comprises a solution of water and diethanolamine.

27. The process of claim 23 wherein said ethanolamine-water solution comprises a solution of water and triethanolamine.

28. The process of claim 23 wherein said anionic ion-exchange resin contains a quaternary ammonium functional group as the active ion constituent.

29. The process of claim 23 wherein said cationic exchange resin comprises sulfonic or carboxylic acid or a mixture thereof.

30. The process of claim 23 wherein said anionic and said cationic ion-exchange resins are placed in separate beds, one above the other, in a single vessel.

31. The process of claim 23 wherein said anionic and said cationic ion-exchange resins are placed in separate vessels.

32. The process of 23 further comprising contacting said ethanolamine-water solution with an anionic ion-exchange resin prior to contacting said ethanolamine-water solution with a cationic ion-exchange resin.

33. The process of claim 23 further comprising contacting said ethanolamine-water solution with a cationic ion-exchange resin prior to contacting said ethanolamine-water solution with an anionic ion-exchange resin.

34. A process for removing salts from an ethanolamine-water solution having ethanolamine concentration sufficient for effective sorption of acid gases comprising the steps of:
  (a) filtering said ethanolamine-water solution to remove suspended particulate;
  (b) contacting said filtered ethanolamine-water solution with an anionic ion-exchange resin;
  (c) contacting said ethanolamine-water solution with a cationic exchange resin;
  (d) regenerating said ion-exchange resins in-situ to restore the ion exchange capacity of said ion-exchange resins while minimizing accumulation of heat stable salts in said ethanolamine-water solution by
    (i) contacting said anionic ion-exchange resin with an aqueous solution of $(NH_4)_2HCO_3$, $NH_4HCO_3$, $NH_4OH$, or a mixture thereof whereby counter ions are deposited on said anionic ion-exchange resin;
    (ii) separating said solution from said anionic ion-exchange resin;
    (iii) contacting said cationic ion-exchange resin with said aqueous solution of $(NH_4)_2HCO_3$, $NH_4HCO_3$, $NH_4OH$, or a mixture thereof whereby counter ions are deposited on said cationic ion-exchange resin;
    (iv) separating said cationic ion-exchange resin from said solution; and
    (v) recycling at least a portion of said ethanolamine-water solution to steps (b) and (c) for contact with said regenerated ion-exchange resins of step (d) in the absence of an ion exchange resin rinsing step for removing residual regeneration solution from said ion-exchange resin whereby said counter ions are removed from said ion exchange resins by exchange with impurities in said ethanolamine-water solution; and
    (vi) stripping said counter ions from said ethanolamine solution whereby heat stable salt content is reduced as compared to the same method using other caustic regenerants.

35. A continuous process for purifying a gas stream containing $CO_2$, $H_2S$ or both, comprising the steps of:
  (a) contacting said gas stream with an ethanolamine-water solution, said ethanolamine-water solution having ethanolamine concentration sufficient for effective sorption of $CO_2$, $H_2S$ or both;
  (b) contacting said ethanolamine-water solution with an anionic ion-exchange resin;
  (c) contacting said ethanolamine-water solution with a cationic exchange resin;
  (d) regenerating said ion-exchange resins in-situ with an aqueous solution of $(NH_4)_2HCO_3$, $NH_4HCO_3$, $NH_4OH$, or a mixture thereof to minimize accumulation of heat stable salts in said ethanolamine-water solution whereby counter ions are deposited on said anionic and said cationic exchange resins; and
  (e) repeating steps (a), (b), and (c) with the provisoes that steps (b) and (c) are conducted with the regenerated ion-exchange resins of step (d), that at least a portion of said ethanolamine-water solution is recycled to step (a), that said counter ions are removed from said ion exchange resins by exchange with impurities in said ethanolamine-water solution, that the regenerated ion-exchange resins of step (d) are not rinsed to remove said aqueous solution of step (d), and that said counter ions are subsequently stripped from said ethanolamine-water solution whereby heat stable salt content is reduced as compared to the same method using other caustic regenerants.

36. The process of claim 35 wherein the total concentration of $(NH_4)_2HCO_3$, $NH_4HCO_3$, and $NH_4OH$ ranges from about 0.1 to about 5 moles per liter.

37. The process of claim 35 wherein the total concentration of $(NH_4)_2HCO_3$, $NH_4HCO_3$, and $NH_4OH$ ranges from about 0.5 to about 2 moles per liter.

38. A continuous process for purifying a gas stream containing $CO_2$, $H_2S$ or both, comprising the steps of:
  (a) splitting said gas stream into a bypass stream and a slip stream, said slip stream comprising between 0 and 100% of the total mass flow of said gas stream;
  (b) contacting said slip stream with an ethanolamine-water solution, said ethanolamine-water solution having ethanolamine concentration sufficient for effective sorption of $CO_2$, $H_2S$ or both;
  (c) contacting said ethanolamine-water solution with an anionic ion-exchange resin;
  (d) contacting said ethanolamine-water solution with a cationic ion-exchange resin;
  (e) regenerating said ion-exchange resins in-situ with an aqueous solution of $(NH_4)_2HCO_3$, $NH_4HCO_3$, $NH_4OH$, or a mixture thereof to minimize accumulation of heat stable salts in said ethanolamine-water solution; and
  (f) repeating steps (c) and (d) with the provisoes that steps (c) and (d) are conducted with the regenerated ion-exchange resins of step (e), that at least a portion of said ethanolamine-water solution is recycled to step (b), that said counter ions are removed from said ion-exchange resins by exchange with impurities in said ethanolamine-water solution, that the regenerated ion-exchange resins of step (d) are not rinsed to remove said aqueous solution of step (d), and that said counter ions are subsequently stripped from said ethanolamine-water solution whereby heat stable salt content is reduced as compared to the same method using other caustic regenerants.

* * * * *

UNITED STATES PATENT AND TRADEMARK OFFICE
CERTIFICATE OF CORRECTION

PATENT NO. : 5,268,155
DATED : December 7, 1993
INVENTOR(S) : T. Y. Yan

It is certified that error appears in the above-indentified patent and that said Letters Patent is hereby corrected as shown below:

Col. 5, line 52, insert --a-- before "mixture"

Col. 6, line 58, after "resin" insert --;-- and delete "with"

Signed and Sealed this

Thirty-first Day of May, 1994

Attest:

BRUCE LEHMAN

*Attesting Officer*   *Commissioner of Patents and Trademarks*